United States Patent
Hagen et al.

(10) Patent No.: US 11,980,731 B2
(45) Date of Patent: May 14, 2024

(54) ENEMA NOZZLE AND AN ENEMA DEVICE COMPRISING SAID ENEMA NOZZLE

(71) Applicant: Qufora A/S, Allerød (DK)

(72) Inventors: Thit Rose Hagen, Roskilde (DK); Henrik Bork Bjerregaard, Lynge (DK); Ole Hougaard, Helsingør (DK); Lars Monroy, Bagsværd (DK)

(73) Assignee: Qufora A/S, Allerød (DK)

( * ) Notice: Subject to any disclaimer, the term of this patent is extended or adjusted under 35 U.S.C. 154(b) by 0 days.

(21) Appl. No.: 18/007,850

(22) PCT Filed: Jun. 1, 2021

(86) PCT No.: PCT/EP2021/064656
§ 371 (c)(1),
(2) Date: Dec. 2, 2022

(87) PCT Pub. No.: WO2021/245069
PCT Pub. Date: Dec. 9, 2021

(65) Prior Publication Data
US 2023/0211070 A1 Jul. 6, 2023

(30) Foreign Application Priority Data
Jun. 3, 2020 (DK) .............................. PA202070353

(51) Int. Cl.
*A61M 3/02* (2006.01)

(52) U.S. Cl.
CPC ........ *A61M 3/0279* (2013.01); *A61M 3/0295* (2013.01); *A61M 2205/0216* (2013.01); *A61M 2205/0238* (2013.01)

(58) Field of Classification Search
CPC ............ A61M 3/00; A61M 3/02–3/06; A61M 3/0279–3/0295
See application file for complete search history.

(56) References Cited

U.S. PATENT DOCUMENTS

| | | | |
|---|---|---|---|
| 4,333,460 A | 6/1982 | Miller | |
| 4,427,012 A | 1/1984 | Miller | |
| 2005/0004533 A1 | 1/2005 | Smith | |
| 2005/0090786 A1 | 4/2005 | Moon | |
| 2006/0253087 A1* | 11/2006 | Vlodaver | A61M 3/0287 604/212 |
| 2009/0171268 A1 | 7/2009 | Williams, Jr. et al. | |
| 2013/0110157 A1* | 5/2013 | Sherman | A61M 25/008 606/213 |

FOREIGN PATENT DOCUMENTS

| | | |
|---|---|---|
| CN | 202211893 U | 5/2012 |
| CN | 109077922 A | 12/2018 |

(Continued)

*Primary Examiner* — Brandy S Lee
*Assistant Examiner* — Hong-Van N Trinh
(74) *Attorney, Agent, or Firm* — Fox Rothschild LLP

(57) ABSTRACT

Provided is an enema nozzle for an enema device. Said enema nozzle includes an insertion body with a flexible insertion tip. The flexible insertion tip is located at the insertion end of the insertion body, and said tip will flex when it abuts intestinal tissue. This will provide a smoother insertion, which effectively will alleviate the physical discomfort and pain that a patient may expire during insertion of an enema nozzle.

14 Claims, 5 Drawing Sheets

(56) References Cited

FOREIGN PATENT DOCUMENTS

| CN | 208552673 U | | 3/2019 | |
|---|---|---|---|---|
| CN | 209422616 U | | 9/2019 | |
| CN | 209713820 U | | 12/2019 | |
| GB | 2472367 A | | 2/2011 | |
| GB | 2563933 A | * | 1/2019 | ............ A61M 25/04 |
| GB | 2563933 A | | 1/2019 | |
| WO | 2018/077361 A1 | | 5/2018 | |
| WO | 2018/085196 A1 | | 5/2018 | |
| WO | WO-2018085196 A1 | * | 5/2018 | ............. A46B 5/005 |
| WO | WO-2019038791 A1 | * | 2/2019 | ........... A61M 3/0208 |

\* cited by examiner

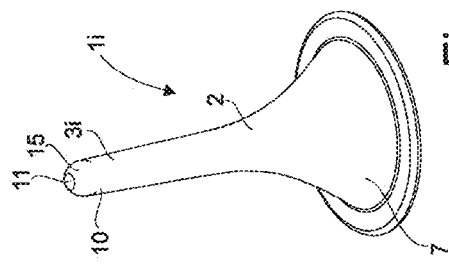
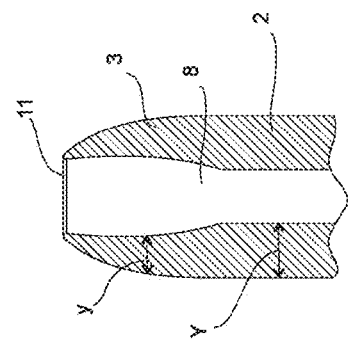
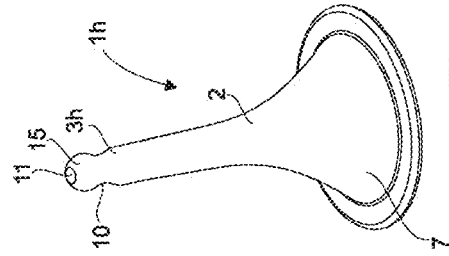
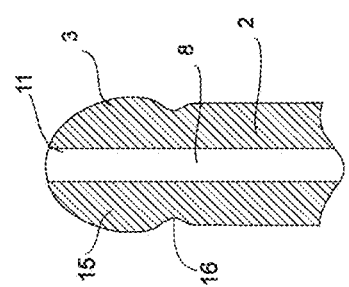
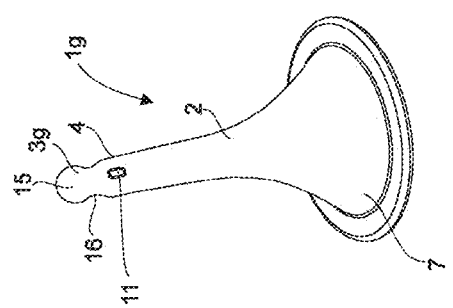

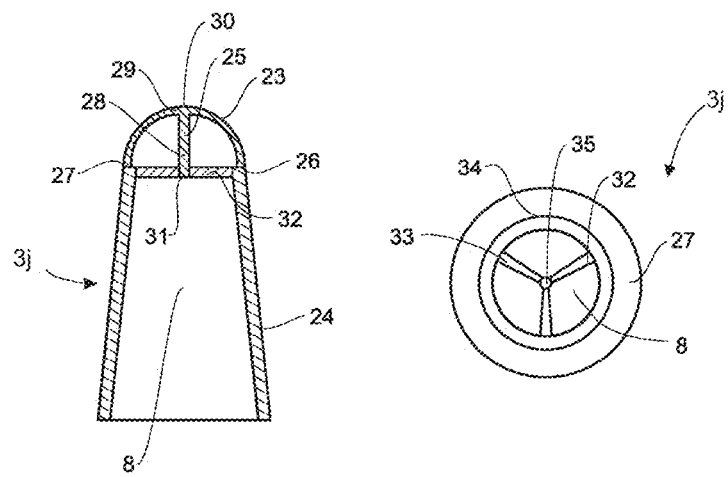
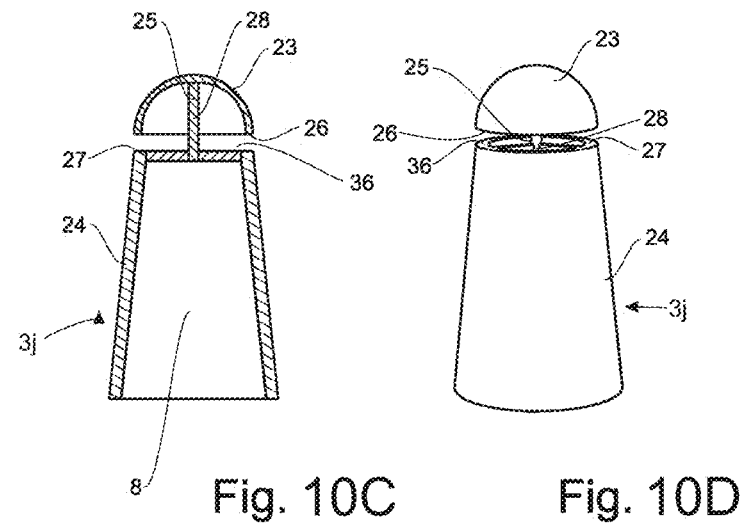
Fig. 10A  Fig. 10B
Fig. 10C  Fig. 10D

ENEMA NOZZLE AND AN ENEMA DEVICE COMPRISING SAID ENEMA NOZZLE

CROSS REFERENCE TO RELATED APPLICATIONS

This application is a 371 filing of International Patent Application PCT/EP2021/064656 filed Jun. 1, 2021, which claims the benefit of priority to Danish patent application no. PA 2020 70353 filed Jun. 3, 2020, the disclosures of which are hereby incorporated by reference herein.

TECHNICAL FIELD

The present invention relates to an enema nozzle for delivering an enema, and an enema device comprising said enema nozzle.

BACKGROUND

Administrating an enema is a common medical procedure whereby fluid is injected into the rectum and lower intestine of a patient in order to induce bowel movement. The need for such a procedure typically arises in patients suffering from certain physical ailments in which voluntary bowel control is impaired or when the bowel needs to be cleaned before e.g., a coloscopy or a surgical operation.

Enemas are often administered to a patient at home when the need for medical assistance does not necessitate a doctor or another health care assistant. However, it is often difficult for the patient to administer the enema to him or herself since the applicator nozzle must be inserted into a small, sensitive area, either via the anus or a stoma, or alternatively inserted into a fistula.

In order to make the insertion easier, the enema nozzles have conventionally been made from a relatively stiff material, thereby providing the longitudinal rigidity and strength required for easily advancing the nozzle in the body opening, e.g., by pushing on an exterior end of the enema device.

However, frequent use of such stiff enema nozzles have been known to cause problems. For instance, when a standard enema nozzle is introduced in the colon through the rectum, the relatively rigid tip of the conventional enema devices have a tendency to intercept e.g., hemorrhoids, fistulas, and/or abscesses the patient may have at the insertion site, whereby the user must apply a certain amount of force to bypass said obstacles. This will not only make the insertion process difficult and painful, but said process may furthermore cause injuries and/or traumas to the colon walls, which may be increased if the patient e.g., suffers from inflammation at the insertion site.

SUMMARY OF THE INVENTION

It is therefore a first aspect of the present invention to provide an enema nozzle arranged for being connected to an enema device, which nozzle that can be inserted into an opening to be irrigated, without causing discomfort, trauma and/or injuries.

It is a second aspect of the present invention to provide an enema nozzle which can be used without the addition of a lubricant.

It is a third aspect of the present invention to provide an enema nozzle that is inexpensive to manufacture and is simple and reliable to use.

It is a fourth aspect of the present invention to provide an enema nozzle that is relatively small and easy to operate.

These and further aspects are achieved according to the present invention by providing an enema nozzle for an enema device, and wherein said enema nozzle comprises an insertion body with a flexible insertion tip.

The flexible insertion tip is located at the insertion end of the insertion body, and since said tip is flexible the tip will flex when it abuts intestinal tissue. This will provide a smoother insertion, which effectively will alleviate the physical discomfort and pain that a patient may expire during insertion of an enema nozzle. The flexible insertion tip will accordingly ensure that the injuries to the rectum and colon walls are minimized. It is known that repetitive tissue trauma, which are not allowed time to heal, can result in more serious conditions and the enema nozzle according to the invention expediently reduces this risk. Repetitive enema administrations can thereby be performed without inflicting trauma to surrounding tissue.

Within the context of the present invention the term "flexible insertion tip" refers to the distal section/end of the enema nozzle, i.e. the part which is inserted first in the rectum/colon. Said tip is less rigid, i.e. softer, more elastic, and more flexible, than the insertion body, such that said flexible tip may deform and/or flex when it is inserted into the rectum and colon. Said distal section/end may either be a separate part attached to the insertion body, or an integrated part of the insertion body.

In order to permit insertion of the enema nozzle into a body opening, it is in addition to providing a flexible insertion tip, relevant that the insertion body has sufficient rigidity to permit insertion through the body opening to be irrigated, e.g., the rectum, and that said insertion body furthermore easily can be advanced into the intestine. This is especially relevant when the intestine/colon comprises one or more restricted areas, e.g., caused by the anatomy of the colon and/or by anal and rectal disorders such as hemorrhoids, fistulas, abscesses and the like. It is accordingly preferred that the insertion body has a certain degree of flexibility, especially if the enema nozzle is intended for being inserted at a certain depth in the colon.

Thus, in a preferred embodiment the flexibility of the flexible insertion tip is different from the flexibility of the insertion body. The flexible insertion tip is preferably at least twice as flexible as the insertion body, even more preferred at least five times as flexible as the insertion body and even more preferred at least ten times as flexible as the insertion body.

Such a construction will impart both a high degree of flexibility to the flexible insertion tip and the desired strength to the insertion body, and will accordingly ensure an easy insertion onto e.g., the rectum while preventing damage to the colon/rectal tissue.

It is in this respect preferred that the flexible insertion tip has a shore A hardness from 30 to 80 as measured in accordance with ASTM D2240. The inventors of the present invention has in this respect found that if the flexible insertion tip has a shore A hardness outside this range, the flexible insertion tip will either not have sufficient rigidity to permit insertion through the rectum and/or not have the desired flexibility to provide a smooth transit over the tissue it encounters during insertion. The best results have been provided when the flexible insertion tip has a shore A hardness from 40 to 70, preferably about 60.

The flexibility/elasticity of the insertion tip may be constant over the longitudinal length of the flexible insertion tip. However, in an alternative embodiment the flexibility/elasticity of the insertion tip is different along the longitudinal length of said tip, e.g., such that the flexibility of the insertion tip increases or decreases, gradually or in steps, toward its distal end.

It is further preferred that the insertion body has a shore A hardness above 100, as measured in accordance with ASTM D2240, more preferably above 150 and even more preferred above 250, as such an insertion body has proven to provide the desired degree of strength and flexibility.

In order to provide the desired combination of rigidity/flexibility of the enema nozzle, said flexible insertion tip and/or the insertion body, or at least a part of said insertion body, may be made of a polymer. Suitable materials in this respect are elastomeric polymers, preferably selected from the group consisting of thermoplastic elastomers (TPE), polyurethane (PU), polyethylene (PE), polyvinyl chloride (PVC), silicone, styrene ethylene butylene styrene (SEBS), thermoplastic polyester elastomer (TPC), thermoplastic styrenic elastomer (TPS), and other similar polymers. The flexibility of the flexible insertion top and the insertion body respectively, can accordingly be altered, e.g., by changing the length of the polymer chains, creating branched chains from linear polymer chains, cross linking the polymer chains and/or adding plasticizers into the polymer.

The inventors of the present invention has found that inserting the enema nozzle according to the present invention into a body opening e.g., the rectum, requires significantly less force than inserting a conventional enema nozzle, and the present enema nozzle is therefore especially advantageously for disabled patients and/or patients suffering from an impairment e.g., relating to aging, diagnose or trauma. Such patients normally have reduced hand strength and/or dexterity, and the force needed to insert a conventional enema nozzle may have the consequence that the user is no longer able to use the device him- or herself. This is remedied by the present enema nozzle, which therefore both is excellently suited for use at home, and in situations where the insertion of an enema nozzle normally would have been affected by conditions at the insertion site, e.g., obstructions such as fistulas or abscesses.

The enema nozzle preferably comprises at least one flow channel extending into at least one delivery opening for delivering/expelling the enema. Said delivery opening(s) may be placed at the distal end of the insertion body, just below e.g., substantially adjacent, the flexible insertion tip. Thereby the flexible insertion tip will function independently of the enema flow, but the delivery opening(s) are still placed at the distal end of the enema nozzle. Such a configuration may also be particularly desirable where the user's rectum or colon is inflamed or otherwise sensitive to contact by a pressurized stream of enema.

Said flow channel is preferably placed inside a substantially tubular section of the insertion body. In a preferred embodiment the flow channel is a tube extending in the longitudinal direction of said insertion body. The proximal end said flow channel is preferably arranged for being connected to an enema device, such as an enema reservoir and/or enema pump via conventional coupling means and the distal end of said one or more flow channels are ending in at least one delivery opening for delivering/expelling the enema.

In some embodiments it may however be preferred to place said at least one delivery opening at the flexible insertion tip, e.g., at the end of said tip, e.g., in order to provide a short enema nozzle. This may easily be obtained simply by extending the one or more interior flow channels into the flexible insertion tip. It is however preferred that said flow channels in these embodiments exhibit the same flexibility as the flexible insertion tip, in order to provide the desired flexibility of the flexible insertion tip.

The flexible insertion tip may be provided in a number of ways, e.g., by varying the mechanical and/or chemical properties of the flexible insertion tip, bending moment of inertia, or the dimensions of said tip.

It is preferred that the flexible insertion tip and the insertion body are made of the same material as this provides an especially simple and inexpensive embodiment. The flexible insertion tip and insertion body may accordingly be provided as an integrated unit, wherein the flexible insertion tip is provided by mechanically and/or chemically altering a distal section/end of the integrated unit, thereby defining the flexible insertion tip.

For instance, a distal section/end of the integrated unit may be subjected to a chemical treatment arranged for changing the properties of the material, thereby providing the flexible insertion tip. If the inserting body is made of a polymer, e.g., PVC the chemical treatment may be an addition of one or more plasticizers to the distal section/end of the integrated unit, thereby providing a more elastic, flexible and softer distal section/end which thereafter defines the flexible insertion tip. The addition of plasticizers into a polymer also increases the free volume of the polymer, causing them to have lower glass transition temperatures, which also plays a part in the polymer becoming softer.

The chemical treatment may the same over the entire flexible insertion tip, such that the flexibility of the flexible insertion tip is constant in the longitudinal length of the flexible insertion tip. Alternatively, the chemical treatment may be applied in such a way that the flexibility/elasticity of the insertion tip is different towards its distal end, e.g., such that the flexibility of the insertion tip increases, gradually or in steps, toward the distal end of the flexible insertion tip.

In a different embodiment the flexible insertion tip is a hollow construction, such that the flexible insertion tip comprises a shell having wall, and wherein the thickness of the wall defines the flexibility of the insertion tip. The thickness may be uniform along the longitudinal length of the flexible insertion tip, be irregular, linear, or non-linear e.g., gradually degreasing towards the distal end. If the delivery opening for the enema is placed at the end/tip of the flexible insertion tip, the flow channel for the enema will extend through both the insertion body and the flexible insertion tip preferably in such a way that the hollow interior of the flexible tip will constitute a part of said flow channel. In such an embodiment the wall thickness of the flexible insertion tip is preferably smaller than the wall thickness of the insertion body.

In an alternative embodiment the flexible insertion tip comprises a head portion and a stem portion, and wherein said stem portion has a smaller diameter than the insertion body and/or the head portion. By simply altering the cross sectional geometry of the stem portion relative to the insertion body and/or head portion if the flexible insertion tip, the flexible insertion tip's bending moment of inertia is altered thereby providing the desired flexibly to the insertion tip.

By providing a high degree of flexibility to the stem portion by reducing the diameter, the head portion of the flexible insertion tip can easily conform to differences in the irregular surface area of colon tissues and/or contracting or moving tissues.

The inventors of the present invention has found that if the stem portion has a diameter which is between 0.20 and 0.5 times the diameter of the head portion and/or the insertion body, the flexible insertion tip will have both the desired flexibility for flexing upon contact with the intestinal tissue, and maintain sufficient rigidity for the enema nozzle to be easily inserted into the rectum and colon.

Alternatively, the flexibly insertion tip may be obtained by e providing one or more elongated grooves defining gaps in the exterior wall of the insertion body/integrated unit. Thereby is the required flexibility to the insertion tip provided, which more capably conforms to and bypass body tissues that may have an irregular surface area.

Said elongated grooves may have various shapes and sizes, but in one preferred embodiment a number of annular or ring-like surface grooves may be cut or otherwise formed into the exterior sidewall of the flexible insertion tip. The grooves define areas of decreased wall thickness and decreased cross-sectional area of the sidewall, and hence the areas of the wall occupied by the elongated grooves are structurally weaker and less rigid than areas of the sidewall where the grooves are not present, thereby imparting the desired flexible properties to the flexible insertion tip.

The respective grooves may be spaced equidistant from each other along a longitudinal length of the flexible insertion tip, — or be concentrated at one or more areas of said tip. In a preferred embodiment the grooves are concentrated at a transition section between the insertion body and the flexible insertion tip, such that said section provides the required flexibility to the insertion tip.

The one or more grooves may extend generally parallel to one another, and each groove may extend in a plane that is generally perpendicular to a longitudinal axis of the flexible insertion tip. In one embodiment, the flexible insertion body comprises one or more grooves forming a continuous 360-degree loop providing a helical configuration along the flexible insertion tip.

The grooves further have the advantage that the grooves may function a lubricant deport, if a lubricant is added before insertion, thereby aiding the insertion of the nozzle in the rectum by reducing frictional force.

In a preferred further embodiment, the flexible insertion tip is divided into a dome and a lower section, and wherein the dome is arranged for being separated (raised) from the lower section by the pressure/force applied to the dome by the enema during administration of the enema.

When the dome separates from the lower section, a gap (delivery opening) is provided between a lower circumferical edge of the dome and a top circumferical edge of the lower section through which the enema may be expelled.

In order to prevent the dome from being completely separated from the lower section of the flexible insertion tip, said dome is connected to the lower section via an elastic attachment unit, which may comprise at least one elastic string and a net/grid. Said at least one elastic string and said net/grid will in combination substantially prevent relative movements, especially lateral movements, of the dome and firmly connect the dome and the lower section to each other. In a preferred embodiment, the elastic attachment unit is integrated with the dome and/or lower section, thereby providing a safe, simple, and secure enema nozzle according to the invention.

Preferably, the elastic attachment unit comprises a single elastic string. Said string may at one end be attached to the top op the dome, and at the other end to the net/grid, which is connected to the lower section. The net/grid may be made of a number of connecting members with little or no elasticity for securely holding the string, and accordingly the dome in place.

During insertion of the enema nozzle, the flexible insertion tip is arranged such that it will flex when it abuts intestinal tissue. However, since the dome and the lower section of the flexible insertion tip abut against each other during the insertion, there will be no sharp edges that may cause harm or irritation to the colon tissue during insertion. When the enema nozzle has reached the desired insertion depth, the user will initiate an enema flow through the nozzle, which upon contact with the dome, will force the lower circumferical edge of the dome to separate from a top circumferical edge of the lower section, thereby proving a gap/opening, extending along the entire circumference of the insertion body, through which the enema can be expelled into the body opening. The extend that the dome and the lower section is separated, is determined by the length and elasticity of the elastic attachment unit. However, in a preferred embodiment a gap/opening of about 1-5 mm is provided, taken in the longitudinal direction of the enema nozzle.

When the flow of enema through the enema nozzle is stopped, the elasticity of the least one elastic attachment unit, e.g., the elastic string, will pull the dome back into the initial position, in which there is no gap between the dome and lower section, and the nozzle can be removed.

Even though it is preferred that the insertion body and flexible insertion tip are made of the same material, the flexible insertion tip may also be made of a different material than the insertion body. This may be two different polymers, or polymers having different molecular weight, different length, and degree of branching of the polymer chains, etc.

A person skilled in the art will based on the teaching in the present application understand, that the flexible insertion tip e.g., the flexible insertion tip described in relation to the above embodiments, also can be made as a separate unit, and attached to the insertion body by suitable attachment means, e.g., welding, adhesive etc. Such embodiments are especially preferred if the insertion body is made of a rigid or substantially rigid material, and/or if the desired flexibility can not be made by altering a distal section/end of insertion body.

In order to ensure that the flexible insertion tip easily can bypass any irregularities in the colon tissues without causing harm to said tissue, it is preferred that the flexible insertion tip comprises a rounded spherical head region, which may have a diameter which is substantially the same or slightly greater than the diameter of the insertion body. It is in this resects preferred that the diameter of the rounded spherical head region is between 1.0 and 1.3 times the diameter of the insertion body taken at a cross section adjacent the flexile insertion tip, preferably between 1.05 and 1.15 times the diameter of the insertion body.

The enema nozzle according to the invention may have any desired shape and dimensions. However, in a preferred embodiment, the insertion body is a substantially elongate tubular part having a proximal end that extends into a flared funnel-shaped part, preferably via a smooth transition. The flared funnel-shaped part is preferably arranged for providing a sealing effect with the rectum.

The insertion body may have any suitable length, depending on the intended delivery site of the enema in the colon, the longer the insertion part the further into the colon the enema may be delivered.

In one preferred embodiment the insertion body is relatively short i.e. arranged for delivering the enema in the areas just inside the rectum. In such an embodiment the total length of the flexible tip and insertion body is preferably less than 9 cm, preferably less than 7 cm and even more preferred around or less than 5 cm.

The enema nozzle may comprise other features, e.g., a number of one-way valves for preventing back flow into the nozzle, an expandable fixation member in form of a balloon for retaining the nozzle in the rectum during injection, etc. Said balloon can be inflated with air or a liquid after the insertion of the tube. In a preferred embodiment the enema nozzle according to the invention does not comprise any fixation member(s), e.g., in the form of a flexible skirt, however if the enema nozzle comprises a fixation member, said fixation member is preferably an expandable balloon located after the flexible insertion tip. In such cases the flexible insertion tip is inserted before the fixation member in the body opening, i.e. the flexible insertion tip and the fixation member are two different parts of the enema nozzle.

In addition the flexible insertion tip and at least the part of the insertion body intended for being inserted into the body opening, may be coated with a hydrophilic coating, for example either as a full coverage coating or an island coating consisting of hydrophilic dots separated by not-coated areas.

When the hydrophilic coating gets wet, e.g., simply when contacted with water, saline or other liquid swelling medium prior to inserting the enema nozzle, the hydrophilic coating gels and/or swells and confers a friction-reducing surface to the exterior face of the coated section or coated part of the nozzle, thereby aiding in enabling a gentle insertion of the nozzle into e.g., the rectum. The swelled hydrophilic coating is resilient and flexible and this characteristic, together with the remaining liquid absorbing properties of the hydrophilic coating, makes the hydrophilic coating also act as an effective seal against leakage along the length of the tubular distal part and out of the rectum or other body cavity.

The enema nozzle according to the present invention may be manufactured using any conventional process. It is however preferred that the enema nozzle is manufactured in a single injection molding procedure by 1K injection molding, 2K injection molding or 3K injection molding.

2K or 3K injection molding consists of processing two or three different polymers (or polymer compositions) into an end product by means of one injection molding process. With the 2K and 3K technique a possible assembly step is prevented. The choice for a 2K or 3K injection molding process is primarily based on a cost advantages, design features or aesthetic preferences.

This technology enables a simple and effective manner of integrating the properties of the polymers into the enema nozzle according to the invention. For instance, the 2K injection molding process can be used to combine two different elastomeric polymers with different properties, e.g., one first elastomeric polymer that will form the insertion body and one second elastomeric polymer that will form the flexible insertion tip, and wherein the second elastomeric polymer will be softer, i.e. have a lower shore A hardness, than the first elastomeric polymer.

The 2K or 3K injection molding process is preferably performed on one machine that is programmed to perform the injection of the polymers in a single cycle. The injection molding may either be a co-injection molding process, a sequential injection molding process or an over molding injection process.

The 2K or 3K single injection molding procedure may also be used to apply a hydrophilic coating on the flexible insertion tip, and optionally at least the part of the insertion body intended for being inserted into the body opening. For such an embodiment the enema nozzle may be prepared via a 3K injection molding process in which the flexible insertion tip and the insertion body is first formed in a 2K injection molding procedure (co-injection or sequential injection), and the coating is applied using over molding. In this way an especially simple, cheap and effective process for manufacturing an enema nozzle with a hydrophilic coating is provided.

It is however preferred that the 2K or 3K single injection molding procedure is arranged for combining a polymer, or polymer composition, having intrinsic hydrophilic properties with respectively one (or two) elastomeric polymers having different properties, e.g., thermoplastic elastomer(s) (TPEs). The number of polymer combined in the process depends on whether it is a 2K or 3K injection molding procedure.

The polymer (or polymer composition) having intrinsic hydrophilic properties is preferably used to form/provide at least the flexible insertion tip and the one or two elastomeric polymer(s) may be used to provide the insertion body and/or the flared funnel-shaped part of the insertion body. Optionally also at least the part of the insertion body intended for being inserted into the body opening is made of the polymer having intrinsic hydrophilic properties.

In a preferred embodiment the polymer having intrinsic hydrophilic properties may be the polymer composition described in WO2018/233793 A1. Said application describes a polymer composition with intrinsic hydrophilic properties, which are suitable for manufacturing thermoformed, compression-molded objects presenting hydrophilic external surfaces. Said polymer composition comprises from 10 w/w % to w/w % polyvinylpyrrolidone (PVP) with a Fikentscher's K-value from K10 to K30; from 0 w/w % to 5 w/w % of additives, and from 60 w/w % to 90 w/w % polycaprolactam (PA6) or polycaprolactone (PCL) for balance.

When the hydrophilic coating or polymer having intrinsic hydrophilic properties comes into contact with a liquid, e.g., water or saline, it will provide a friction-reducing surface to the exterior face of the enema nozzle, thereby aiding in enabling a gentle insertion of the nozzle into e.g., the rectum.

The enema nozzle is arranged for being connected to any suitable delivery container, e.g., a delivery container in a large bed-side irrigation system for the use in medical or hospital facilities and/or a small compact delivery container for home-administration of enema. The nozzle may be removable connected to the delivery container by means of conventional coupling unit. Said coupling unit can e.g., comprise a first coupling part attach to the enema nozzle and a second coupling part attached to the delivery container for providing a fluid communication between the two parts. In an especially simple embodiment the first coupling part is the tube for the first flow channel and the second coupling part is a second tube on the delivery container. Said second tube is preferably adapted for providing a liquid tight fit together with the first tube in order to provide the coupling, e.g., by providing that at least one of the first and second tube is made of a flexible material, such that e.g., the one tube can be placed in the other tube.

The invention will be explained in greater detail below, describing only exemplary embodiments of the enema nozzle with reference to the drawing, in which

BRIEF DESCRIPTION OF THE DRAWINGS

FIG. 7 shows a perspective view of a seventh embodiment of an enema nozzle according to the present invention, FIG. 8A shows a perspective view of an eight embodiment of an enema nozzle according to the present invention, FIG. 8B shows a cross sectional view of the distal end of the enema nozzle shown in FIG. 8A, FIG. 9A shows a perspective view of a ninth embodiment of an enema nozzle according to the present invention, FIG. 9B shows a cross sectional view of the distal end of the enema nozzle shown in FIG. 9A, FIG. 10A-D show different perspectives of a tenth embodiment of an enema nozzle according to the present invention.

DETAILED DESCRIPTION OF THE INVENTION

The invention is described below with the assumption that the enema nozzle is provided as an integrated unit, preferably made of the same material. This assumption is not to be construed as limiting, as the flexible insertion tip and insertion body in the embodiments described below also could be made as separate units/parts, e.g., of different materials, and wherein the separate units/parts are connected to each other by conventional means, e.g., welding, heat etc.

Figure 1:
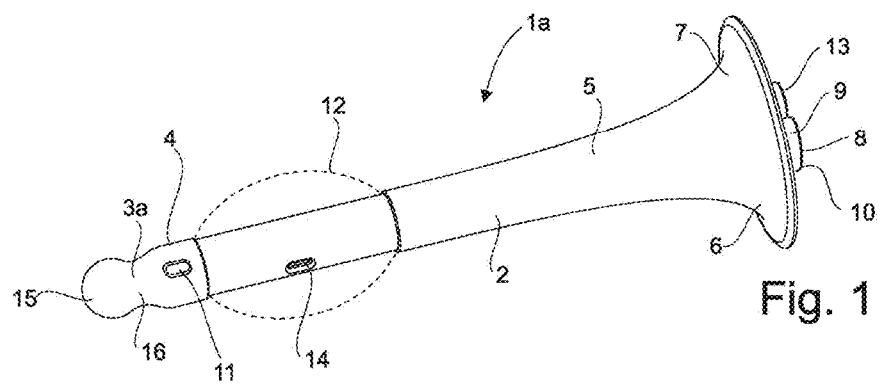
FIG. 1 shows a perspective view of a first embodiment of an enema nozzle according to the present invention.

FIG. 1 is a schematic view of a first embodiment of the enema nozzle 1a according to the invention. Said nozzle 1a consists basically of an insertion body 2 and a flexible insertion tip 3a arranged at the distal end 4 of the insertion body 2. The insertion body 2 is a substantially elongate tubular part 5 having a proximal end 6 that extends into a flared funnel-shaped part 7 via a smooth transition.

The enema nozzle 1a comprises a flow channel 8 for the enema. Said flow channel is a first tube 9 which in the embodiment shown is a tube extending in the longitudinal direction at the inside of the insertion body 2. The tube's proximal end 10 is arranged for being connected to an enema reservoir and/or enema pump (not shown) via a coupling means and the tube's distal end is ending in one or more delivery opening(s) 11 for delivering/expelling the enema. Said delivery opening 11 is placed at the distal end 4 of the insertion body 2, just below the flexible insertion tip 3a. Thereby the flexible insertion tip 3a will operate independently of the enema flow.

In the embodiment shown the enema nozzle also comprises an expandable fixation member in form of a balloon 12, shown in dotted line, for retaining the enema nozzle 1a in the rectum during the enema injection. Said balloon 12 can be inflated with air or a liquid via a second tube 13 ending in an outlet 14. In the embodiment shown said second tube 13 is placed parallel with the first tube 9 for the enema flow, but these tubes 9,13 could also be placed in another mutual relationship, e.g., the first tube inside the second tube.

In FIG. 1 the flexible insertion tip 3a comprises a head portion 15 and a stem portion 16 having a smaller diameter than both the insertion body 2 and the head portion 15. The smaller cross sectional geometry of the stem portion 16 relative to the insertion body 2 and head portion 15, changes the flexible insertion tip 3's bending moment of inertia, providing the desired flexibly to the insertion tip 3a. In this way the flexible insertion tip 3a can easily conform to differences, obstructions, bends etc. when the enema nozzle 1a is introduced in a body opening, e.g., the rectum.

Figure 2:
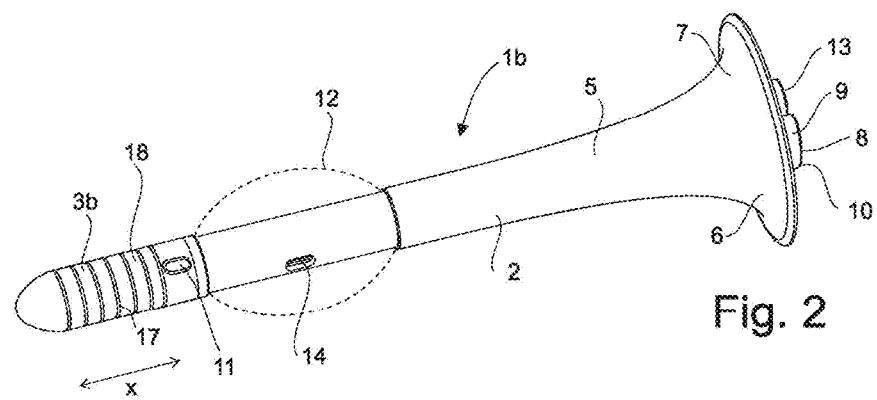
FIG. 2 shows a perspective view of a second embodiment of an enema nozzle according to the present invention.
Figure 3:
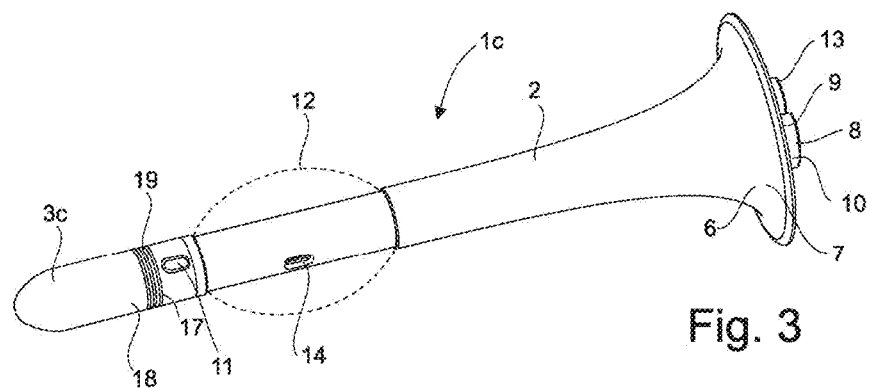
FIG. 3 shows a perspective view of a third embodiment of an enema nozzle according to the present invention.

FIGS. 2 and 3 show a second and third embodiment of the enema nozzle according to the invention, 1b and 1c, respectively. Said embodiments correspond to the embodiment of FIG. 1, except for the construction of the flexile insertion tip 3, and for like parts the same reference numbers are used. In FIGS. 2 and 3 the flexible insertion tips, 3b and 3c are respectively obtained by providing a number of elongated grooves 17.

In both FIGS. 2 and 3 the enema nozzle 1b,1c is made as an integrated unit, and the grooves 17 are made in an exterior wall 18 of the distal end 4 of said integrated unit, thereby providing the flexible insertion tip 3b,3c. However, if the flexible insertion tip and insertion body were separate units, said grooves could also be made in an exterior wall of the flexible insertion tip e.g., the proximal end. The grooves 17 define areas of decreased wall thickness which are structurally weaker and less rigid than areas of the wall 18 where the grooves are not present, thereby imparting the desired flexible properties to the flexible insertion tip 3b,3c.

In FIG. 2 the grooves 17 are spaced equidistant from each other along a longitudinal length X of the flexible insertion tip 3b, and in FIG. 3 the grooves 17 are concentrated in a transition section 19 at the proximal end of the flexible insertion tip, such that said section 19 provides the required flexibility to the flexible insertion tip 3c.

In the embodiments shown in FIGS. 2 and 3 the grooves 17 extend generally parallel to one another, and each groove 17 extends in a plane that is generally perpendicular to a longitudinal axis of the flexible insertion tip. However, other designs and locations of the grooves 17 are also contemplated within the scope of the present invention.

Figure 4:
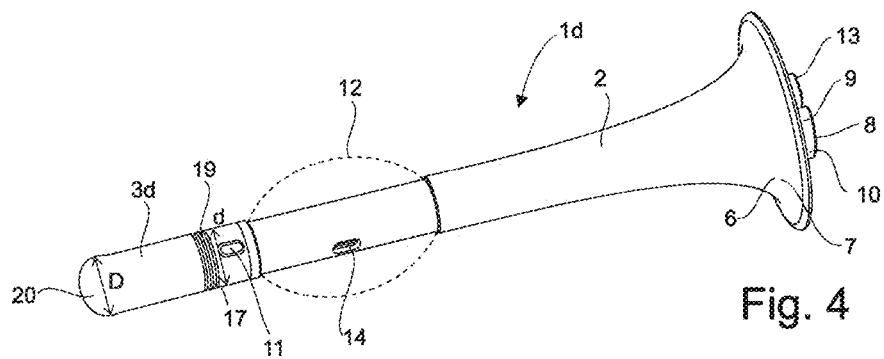
FIG. 4 shows a perspective view of a fourth embodiment of an enema nozzle according to the present invention.

FIG. 4 shows a fourth embodiment 1d of an enema nozzle according to the present invention. Said embodiment corresponds to the embodiment of FIG. 3, with the difference that flexible insertion tip 3d comprises a rounded spherical head region 20, which may have a diameter D which is substantially the same or slightly greater than the diameter d of the insertion body 2. Such an embodiment is especially relevant if the body tissue is inflamed or otherwise damaged, as the contact pressure from the flexible insertion 3d will be distributed over a larger area. Such a spherical head region could of course also be placed on the embodiments shown in the other figures.

Figure 5:
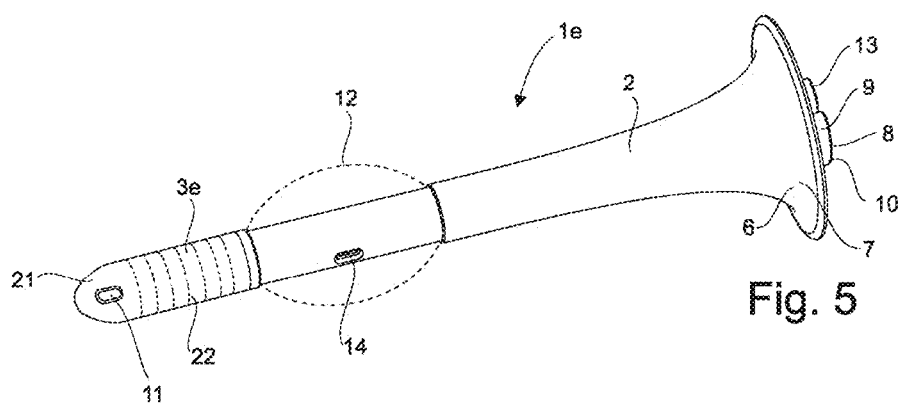
FIG. 5 shows a perspective view of a fifth embodiment of an enema nozzle according to the present invention.
Figure 6:
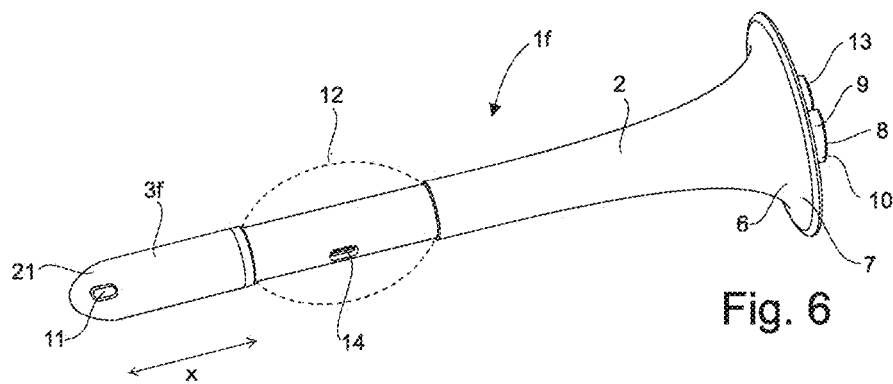
FIG. 6 shows a perspective view of a sixth embodiment of an enema nozzle according to the present invention.

FIGS. 5 and 6 show a fifth and sixth embodiment 1e,1f, of an enema nozzle according to the present invention, having a delivery opening 11 placed in a side wall 21 of the flexible insertion tip 3e,3f. In said embodiments the distal end 4 of the integrated unit is subjected to a chemical treatment, which may be addition of a plasticiser. The properties of the material will be changed by the chemical treatment, thereby providing the flexible insertion tip.

In FIG. 5 the chemical treatment is applied in such a way that the flexibility of the insertion tip 3e either increases or decreases in steps, toward the distal end of the flexible insertion tip 3e, depending on where the flexibility of the insertion tip is desired to be largest. This is illustrated by the dotted lines 22 in FIG. 5.

In the embodiment of FIG. 6 the chemical treatment is the same over the entire flexible insertion tip 3f, such that the flexibility of the insertion tip 3f is constant in the longitudinal length x of the flexible insertion tip 3f.

FIGS. 7 and 8 show a seventh and eight embodiment of the enema nozzle 1g,1h according to the invention. Said two embodiments are basically identical, i.e., they both comprise a flexible insertion tip 3g,3h having a stem portion 16 and a head region 15, as in FIG. 1, the main difference between said embodiments being the location of the delivering opening 11, which in FIG. 7 is placed below (adjacent) the flexible insertion tip 3g, and in FIG. 8A at the end of said tip 3h.

The enema nozzles of FIGS. 7 and 8 do not comprise a fixation member, and may accordingly e.g., be used for a fast and efficient enema procedure, or an enema administration in which the user can maintain the enema device 1 in place during the procedure. Even thought the flexible insertion tip 3g,3h in these embodiments corresponds to the embodiments of FIG. 1, the flexible insertion tips shown in the other figures, FIGS. 1-6, could also be used in an enema nozzle without a fixation member.

FIG. 8B shows a cross section of the distal end of the enema nozzle 1h where the first tube 9 for the enema extends into a delivery opening 11 placed at the end of the flexible tip, i.e., the tube 9 extends through both the head region 15 and stem portion 16.

FIG. 9 shows a ninth embodiment 1i, of the enema nozzle according to the invention in which the first tube 9 also extends into a delivery opening 11 placed at the end of the flexible tip, as in the embodiment shown in FIG. 8A and FIG. 8B. As best shown in FIG. 9B, which is a cross-sectional view of the distal end of enema nozzle 1i, the desired flexibility of the flexible insertion top 3i is provided by gradually reducing the wall thickness y at the flexible tip towards the distal end, and in such a way that the wall thickness y of the flexible insertion tip is smaller than the wall thickness Y of the insertion body 2.

A person skilled in the art will understand that the insertion body 2 of the embodiments shown in the figures can have any desired shape, length and dimension, and that the flared funnel shaped part 7 shown in the embodiments in the FIG. is optional. Furthermore, even though the delivery opening is shown as a round hole in the figures, said opening may have any other relevant shape, e.g., be in the form of one or more elongated slots or slits.

FIG. 10 shows a tenth embodiment of a flexible insertion tip 3j according to the invention, in which the flexible insertion tip is, divided into a dome 23 and a lower section 24, connected by an elastic attachment unit 25.

FIG. 10a is a cross-sectional view taken in the longitudinal direction of the enema nozzle and shows the insertion tip 3j in an insertion position, where the lower circumferical edge 26 of the dome 23 abuts the top circumferical edge 27 of the lower section 24, i.e., no sharp edges that may cause harm or irritation to the colon tissue during insertion is provided.

The elastic attachment unit 25 comprise an elastic string 28 which at one end 29 it integrated with a top section 30 of the dome 23, and at the other end 31 a grid 32. Said grid is best seen in FIG. 10b, which is an upper view showing the inside of the flexible insertion tip 3j, but with the dome 23 and elastic string 28 removed. The grid consists of three connecting members 33, with little or no elasticity. Said connecting members 33 is evenly distributed along the inner circumference 34 of the lower section 24 and intersects in a centre point 35 where the other end of the 31 of the string 28 is attached/integrated. The elastic string 25 and grid 32 will in combination substantially prevent relative movements, especially lateral movements, of the dome and firmly combine the dome and the lower section.

As is best seen in FIGS. 10b and 10c, when the user initiate an enema flow through the enema flow channel 8, said enema will which upon contact with the dome 23, force the lower circumferical edge 26 of the dome 23 to separate from the top circumferical edge 27 of the lower section 24, thereby proving a gap (delivery opening) 36, extending along the entire circumference of the insertion tip 3j, through which the enema can be expelled into the body opening.

The flexibility of the insertion tip 3j is provided by chemical treatment but could be provided as disclosed in any of the other embodiments.

Figure 11:
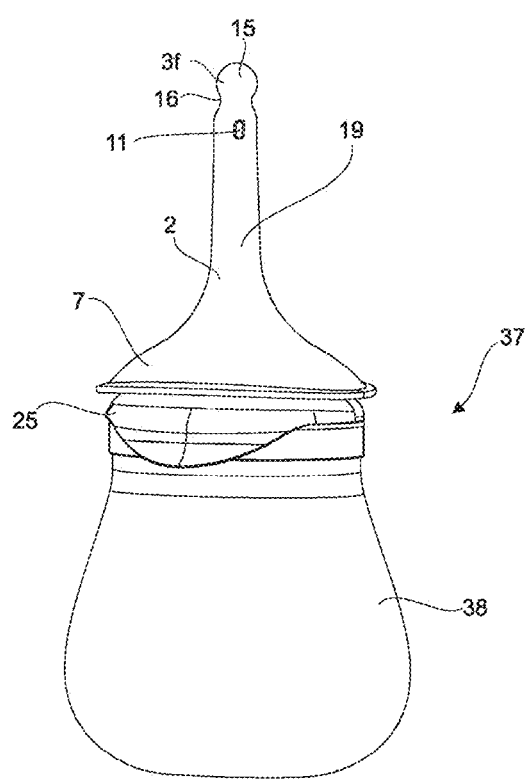
FIG. 11 shows a perspective view of an enema device comprising the enema nozzle shown in FIG. 7.

FIG. 11 shows an enema device 37 according to the invention, wherein the enema nozzle 1g shown in FIG. 7 is connected to a substantially bulb-formed enema delivery container 38, arranged for containing the enema. The enema is administered by squeezing the delivery container 38 one or more times, depending on the desired dosage. The enema device 38 may comprises a one-way valve (not shown) that effectively will prevent backflow of liquid and faeces from the colon and/or rectum into the device 37 and said one-way valve will therefore preclude any contamination of the delivery container 38 and its remaining content, which may occur after administration of the enema to a patient. Furthermore, since backflow efficiently is prevented, the delivery container 38 can easily be used for several applications, e.g., by refilling the container with a second dose of the same—or a different—enema (liquid).

The enema nozzle, 1g, may be removable connected to the delivery container 38 by means of a coupling 39. Thereby can the enema nozzle 1g be a disposable nozzle or the nozzle can be individually cleaned and/or sterilised, and the delivery container 38 may be reused several times.

The enema nozzle 1a-1i may also be used for larger irrigations systems wherein the enema nozzle 1a-1i is connected to the enema reservoir via a relatively long delivery tube, and wherein the irrigation system e.g., comprises pumping means, control means, collection means for the stool, etc.

Modifications and combinations of the above principles and designs are foreseen within the scope of the present invention.

The invention claimed is:

1. An enema nozzle for an enema device, said enema nozzle comprising an insertion body and a flexible insertion tip, wherein the flexible insertion tip has a shore A hardness from 30 to 80 and the insertion body has a hardness above a shore A hardness 100, wherein the flexible insertion tip comprises a head portion and a stem portion more proximal than the head portion to the insertion body, and wherein said stem portion has a smaller diameter than the insertion body and/or the head portion.

2. The enema nozzle according to claim 1, wherein a flexibility of the flexible insertion tip is different from a flexibility of the insertion body.

3. The enema nozzle according to claim 1, wherein the shore A hardness of the flexible insertion tip is from 40 to 70.

4. The enema nozzle according to claim 1, wherein the flexibility of the flexible insertion tip is different along a longitudinal length (X) of said flexible insertion tip.

5. The enema nozzle according to claim 1, wherein the enema nozzle comprises at least one flow channel having at least one delivery opening for delivering/expelling an enema, and wherein said at least one delivery opening is placed at a distal end of the insertion body, below the flexible insertion tip.

6. The enema nozzle according to claim 1, wherein the flexible insertion tip is a hollow construction.

7. The enema nozzle according to claim 1, wherein the stem portion has a diameter which is between 0.20 and 0.5 times a diameter of the head portion and/or the insertion body.

8. The enema nozzle according to claim 1, wherein the flexible insertion tip is made of a material which is different from the material of the insertion body.

9. The enema nozzle according to claim 8, wherein the flexible insertion tip is a separate part connected to the insertion body by an attachment means.

10. An enema device comprising an enema nozzle according to claim 1.

11. A process for manufacturing an enema nozzle according to claim 1 wherein said enema nozzle is manufactured in a single injection molding procedure by 2K injection molding or 3K injection molding.

12. The process according to claim 11, wherein the 2K or 3K single injection molding procedure combines a polymer having intrinsic hydrophilic properties with one or two elastomeric polymer(s), respectively.

13. The process according to claim 12, wherein the polymer having intrinsic hydrophilic properties is used to form at least the flexible insertion tip and at least a part of the insertion body intended for being inserted into a body opening.

14. The process according to claim 11, wherein a hydrophilic coating is applied to the flexible insertion tip, and at least a part of the insertion body intended for being inserted into a body opening, during the single injection molding procedure.

* * * * *